(12) United States Patent
Daly et al.

(10) Patent No.: US 6,844,553 B2
(45) Date of Patent: Jan. 18, 2005

(54) ABSORPTION SPECTROSCOPY APPARATUS AND METHOD

(75) Inventors: James T. Daly, Mansfield, MA (US); William Andrew Bodkin, Wellesley, MA (US)

(73) Assignee: Ion Optics, Inc., Waltham, MA (US)

( * ) Notice: Subject to any disclaimer, the term of this patent is extended or adjusted under 35 U.S.C. 154(b) by 0 days.

(21) Appl. No.: 10/081,655

(22) Filed: Feb. 22, 2002

(65) Prior Publication Data

US 2002/0185603 A1 Dec. 12, 2002

Related U.S. Application Data

(60) Provisional application No. 60/270,789, filed on Feb. 22, 2001.

(51) Int. Cl.[7] .............................................. G01N 21/35
(52) U.S. Cl. ................... 250/339.07; 356/246; 356/945
(58) Field of Search .................. 250/339.07; 356/246, 356/945

(56) References Cited

U.S. PATENT DOCUMENTS

| | | |
|---|---|---|
| 3,976,883 A | 8/1976 | Krakow |
| 4,322,621 A | 3/1982 | Aagard |
| 4,749,276 A | 6/1988 | Bragg et al. |
| 5,220,402 A | 6/1993 | Harvey |
| 5,440,143 A | 8/1995 | Carangelo et al. |
| 5,459,566 A | 10/1995 | Pearson et al. |
| 5,485,276 A | 1/1996 | Bien et al. |
| 5,714,759 A | 2/1998 | Nelson |
| 5,726,752 A | 3/1998 | Uno et al. |
| 5,731,583 A | 3/1998 | Bailey et al. |
| 5,818,578 A | 10/1998 | Inman et al. |
| 5,838,016 A | 11/1998 | Johnson |
| 5,949,537 A | 9/1999 | Inman et al. |
| 6,249,005 B1 | 6/2001 | Johnson |

FOREIGN PATENT DOCUMENTS

WO        WO 99/28729        6/1999

OTHER PUBLICATIONS

Copy of International Search Report.

*Primary Examiner*—Constantine Hannaher
*Assistant Examiner*—Shun Lee
(74) *Attorney, Agent, or Firm*—McDermott Will & Emery LLP

(57) ABSTRACT

An absorption spectroscopy apparatus having a fluid inlet and a fluid outlet. The apparatus includes a sample cell including an axis, a side wall having at least one curved reflective surface arrayed about the axis and facing inwardly with respect to the cell such that a beam of energy directed against a predetermined location on the reflective surface is reflected back and forth off the reflective surface and remains in substantially the same plane while inside the cell, and at least one port in the sidewall. The apparatus also includes at least one source/detector reflector having a curved profile in a plane extending perpendicular to the axis of the cell. The reflector is positioned with respect to the port of the cell to reflect energy through the port of the cell and against the predetermined location on the reflective surface of the side wall of the cell.

36 Claims, 4 Drawing Sheets

ABSORPTION SPECTROSCOPY APPARATUS AND METHOD

CROSS-REFERENCE TO RELATED APPLICATIONS

The present application claims priority to provisional U.S. patent application Ser. No. 60/270,789, filed on Feb. 22, 2001, which is assigned to the assignee of the present invention and incorporated herein by reference.

BACKGROUND OF THE INVENTION

1. Field of the Invention

The present invention relates generally to spectrophotometric techniques for analyzing the content of a given fluid and, more particularly, to an apparatus for optimizing the sensitivity of such analysis. Even more particularly, the present invention relates to a multi-pass cell useful in absorption spectroscopy.

2. Related Art

Spectroscopy systems and methods are used to analyze the composition of various types of materials, including gases, liquids and the like. Spectroscopy is based on the fact that different chemical compositions absorb energy, e.g., light, at different frequencies, so that measuring the frequency of light passed through a sample can be used to identify which light frequencies were absorbed by the sample and which were not. Thus, the chemicals present in the sample can be readily identified. Spectroscopy systems and methods also can identify the amount of light absorbed by the sample at each given frequency. Thus, the quantity of each chemical present in the chemical composition can be determined. In addition, such analysis can be performed with any one of various different ranges of light such as infrared, ultraviolet and the like, each of which pertains to a separate range of frequencies.

An absorption cell (or resonator) for holding the gas or liquid sample through which light is passed is used to perform spectroscopy analysis in conjunction with suitable spectroscopy equipment, such as a light emitter and a light detector. It has long been realized that to increase the sensitivity in providing both quantitative and qualitative analyses, the light must be passed through a very large percentage of the available sample. Thus, absorption cells have been provided with "folded" light paths, in which mirrors reflect the light back and forth within the cell, such that the light makes multiple passes through the sample. The folded light path increases the optical path length between the light emitter and the light detector to thereby increase the sensitivity of a spectroscopy system incorporating an absorption cell producing a folded light path. Examples of existing "multi-pass" absorption cells are shown in U.S. Pat. Nos. 4,322,621; 4,749,276; 5,220,402; 5,440,143; 5,459,566; 5,485,276; 5,714,759; 5,731,583; and 5,949,537.

While many of the existing "multi-pass" absorption cells are effective in increasing the optical path length without greatly increasing the size or volume of the sample, the throughput (etendue) of these cells can be relatively small. The small throughput limits the amount of light that can be directed through the sample and limits the sensitivity of the resulting measurement.

What is still desire is an improved "multi-pass" absorption cell that causes light to pass through a very large percentage of a sample contained in the cell. Preferably, the improved absorption cell will prevent the loss of significant amounts of light through ends of the cell and increase the throughput of the cell. In addition, the improved cell will preferably be compact, robust, and easier to manufacture.

SUMMARY OF DISCLOSURE

The present invention provides an improved absorption spectroscopy apparatus. The apparatus includes a fluid inlet and a fluid outlet, a sample cell, and at least one source/detector reflector. The sample cell has an axis, a side wall having at least one curved reflective surface arrayed about the axis and facing inwardly with respect to the cell such that a beam of energy directed against a predetermined location on the reflective surface is reflected back and forth off the reflective surface and remains in substantially the same plane while inside the cell, and at least one port in the side wall. The source/detector reflector has a curved profile in a plane extending perpendicular to the axis of the cell, and is positioned with respect to the port of the cell to reflect energy through the port of the cell and against the predetermined location on the reflective surface of the side wall of the cell.

The improved absorption spectroscopy apparatus of the present invention enables energy to be passed through a very large percentage of a sample within the sample cell. The cell is constructed so as to be small and compact while nonetheless enabling the energy to make successive passes through the sample. The curved source/detector reflector prevents a decrease in the throughput of the cell. In addition, the improved apparatus has been found to be robust and easier to manufacture.

According to one aspect of the present invention, the source/detector reflector comprises a segment of a cylinder.

According to another aspect of the present invention, the reflective surface of the side wall of the cell has a circular profile in a plane extending perpendicular to the axis of the cell. According to a further aspect, the reflective surface of the side wall of the cell has a flat profile in a plane extending parallel to the axis of the cell.

According to an additional aspect of the present invention, the port of the side wall of the cell includes inlet and outlet ports, and the source/detector reflector includes separate source and detector reflectors corresponding respectively to the inlet and the outlet ports. According to a further aspect, the apparatus includes a source for directing energy against the source reflector; and a detector for receiving energy from the detector reflector.

According to still another aspect of the present invention, the apparatus includes an intermediate reflector positioned with respect to the port of the cell and the emitter/detector reflector to reflect energy from the emitter/detector reflector through the port of the cell and against the predetermined location on the reflective surface of the side wall of the cell.

According to still another aspect of the present invention, the apparatus includes end walls closing ends of the side wall of the cell. According to one aspect, the end walls have reflective surfaces facing inwardly with respect to the cell. According to another aspect, the end walls include the fluid inlet and the fluid outlet of the apparatus.

According to an additional aspect of the present invention, the side wall is molded. According to still a further aspect, the reflective surface of the side wall is polished.

According to another aspect of the present invention, the cell has a height measured in a direction parallel to the axis substantially equal to a length of a source of the apparatus. According to one aspect, an energy path in the cell is substantially perpendicular to the cell axis.

These and other aspects of the present invention will become apparent to those skilled in the art after a reading of the following description of exemplary embodiments when considered with the drawings.

BRIEF DESCRIPTION OF DRAWINGS

The present invention is described with reference to the accompanying drawings, wherein.

Like reference characters designate identical or corresponding components and units throughout the several views.

DETAILED DESCRIPTION OF EXEMPLARY EMBODIMENTS

Figure 1:
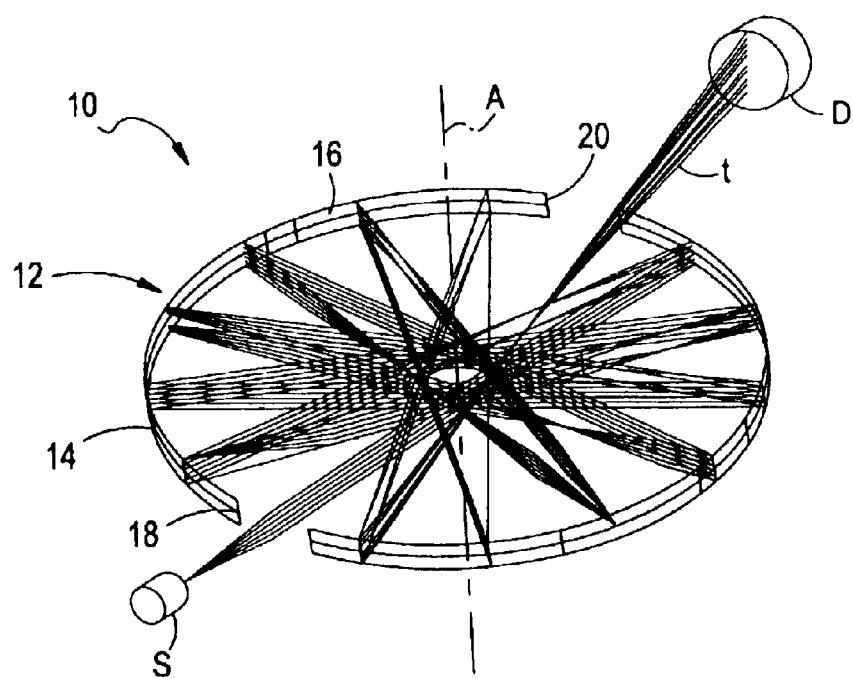
FIG. 1 is a schematic perspective view of a trace of a light ray completing multiple passes through a sample cell of an exemplary embodiment of an improved absorption spectroscopy apparatus constructed in accordance with the present invention.

Referring to FIG. 1 of the drawings, there is shown a schematic representation of an exemplary embodiment of an improved absorption spectroscopy apparatus 10 constructed in accordance with the present invention. The apparatus includes a fluid sample cell 12 having an annular side wall 14 coaxially arranged about an axis "A" of the cell. The side wall 14 includes a radially inwardly facing light reflective surface 16. The light reflective surface 16 is preferably polished metal. If a higher reflectivity of the surface 16 is desirable, the surface can be coated with one or more layers of a reflective material such as gold, other metallic layers or a highly reflective dielectric coating, in order to enhance the reflectivity thereof.

The cell 14 also includes an energy inlet port 18 at one given location in the side wall and an energy outlet port 20 at another given location in the side wall. Although not shown, the cell 12 preferably also includes opposing, flat end walls, which together with the curved side wall form an enclosed cell. The end walls can includes sample inlet and outlet ports that are used to bring fluid samples into the interior cavity and remove the samples from the cell.

In operation, the sample inlet and outlet ports are connected to suitable conduits for delivering fluid samples from a continually operating process or the like. It is contemplated that an absorption spectroscopy apparatus constructed in accordance with the present invention has particular utility in monitoring the content of fluid, such as a gas or liquid, which is passing through a pipe or the like, and that the present apparatus is useful in providing continuous analyses of the contents of gases passing through the pipe. In some cases it may be desirable to maintain the temperature and the pressure within the sample cell at predetermined limits corresponding to the pressure and temperature conditions of the fluid prevailing in the pipe or process (and in some cases to minimize the adverse effects created by deposits formed on the light reflective surface of the side wall). Thus, as the fluid is brought into the sample cell and returned to the original source of such fluid, the original process or other fluid source is in no way affected by the continual spectroscopy analysis. The present invention can be used in many applications including, but not limited to, as a gas analyzer, a replacement for a "White", "Wilks" or "Heriot-Watt" cell resonators, as part of a low-cost engine emissions analyzer, as part of a gas (e.g., carbon monoxide) detector for home or commercial use, as part of a gas leak detector, as part of a breath analyzer, and can be made to be used with liquids.

As energy from an emitter source "S" of the apparatus 10 passes through the energy inlet port 18, the energy is directed to a predetermine point on the inner surface 16 of the curved side wall 14 so as to commence the step-by-step progression of the back-and-forth reflections of such energy through the sample cell 12. FIG. 1 shows a trace "t" of an energy ray completing multiple passes through the enclosed cavity of the sample cell 12. Within the annular configuration of the side wall 14 of the cell 12, the light or energy ray is reflected back-and-forth along the inner surface 16 of the side wall until the energy ray is directed through the energy outlet port 20 in the side wall to a detector "D" for reading the energy absorption that has taken place within the cell. After completing a single revolution of reflections, the light or energy ray thereby passes through substantially all of the gas within the cylindrical cell. The beam residence time and effective path length of the energy ray in the cell sample area is thereby extended. A typical configuration will provided twenty (20) passes of the energy ray across the cell between the energy inlet and outlet ports.

The energy source "S" can comprises an infrared emitter such as the infrared emitters disclosed U.S. Pat. Nos. 5,838, 016 and 6,249,005, and international patent application number PCT/US98/25771 (WO 99/28729), all of which are assigned to the assignee of the present invention and are incorporated herein by reference.

As shown in FIG. 1, the inwardly facing reflective surface 16 of the side wall 14 of the cell 12 has a circular profile as viewed on a plan extending perpendicular with the axis "A". However, the curved side wall can be provided in other profiles, such as elliptical. In addition, the cell can be provided with an inner, outwardly facing, curved reflective surface coaxially arranged within the inwardly facing reflective surface of the side wall. Moreover, the side wall can be provided with a reflective surface having a curved profile as viewed on a plan extending parallel with the axis "A" of the cell.

The cell 12 can also be provided with light transmissive windows positioned in the energy inlet and outlet ports 18, 20. Suitable light transmissive materials for the window are known to those skilled in the art. The light transmissive window in the inlet port can additionally be provided with a coating layer on a surface opposite the surface facing the sample region for reflecting a portion of a light beam.

The curved side wall 14 of the cell 12 of the present invention has been found to be relatively easy and inexpensive to manufacture. In preferred embodiments of the cell 12, the side wall 14 and the end walls are molded, metal stamped or formed using a simple lathe, for example, and secured together in a fluid-tight manner, such as by using bolts and gaskets. The inwardly reflective surface 16 of the side wall 14 and inwardly reflective surfaces of the end walls are preferably polished to produce a high reflectivity.

Although not shown, two or more of such cells 12 can be juxtaposed (e.g., stacked) so as to greatly increase the amount of gas through which the energy passes before it is returned to the detector. In such event, an intermediate reflector(s) may be employed for directing the energy between cells.

Figure 2:
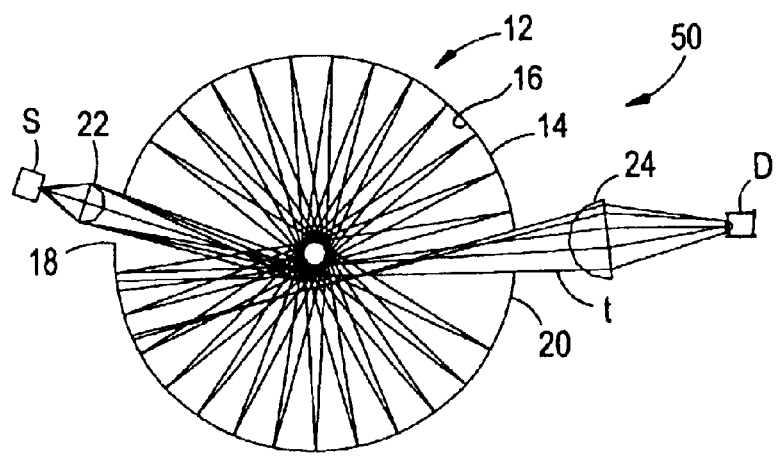
FIG. 2 is a schematic end plan view of a trace of a light ray directed by a set of launch and collection reflectors and completing multiple passes through a sample cell of another exemplary embodiment of an improved absorption spectroscopy apparatus constructed in accordance with the present invention.

Referring to FIG. 2, another exemplary embodiment of a absorption spectroscopy apparatus 50 constructed in accordance with the present invention is shown. The apparatus is similar to the apparatus 10 of FIG. 1 such that similar elements have the same reference characters. However, the apparatus 50 further includes at least one source/detector reflector 22, 24 that has a curved profile in a plane extending perpendicular to the axis of the cell, and is positioned with respect to the ports 18, 20 of the cell 12 to reflect energy through the inlet port of the cell and against the predetermined location on the reflective surface 16 of the side wall 14 of the cell, and receive energy from the outlet port 20. Preferably, the source/detector reflectors 22, 24 each comprise a segment of a cylinder. The curved source/detector reflectors have 22, 24 been found to efficiently collimate the light beam, as the light from the light source is divergent, and thereby increase the throughput of the apparatus 50. It has been found that the solid angle of radiation collected from the source "S" is greatly increased using the cylindrical reflectors 22, 24. In addition, extending the end walls of the cell 12 to cover the ends of the cylindrical reflectors 22, 24 helps to further confine light parallel to the axis "A" of the cell 12 and within the plane of the cell. Furthermore, matching the height of the cell 12 (i.e., distance along the axis "A" and between the end walls) to the source length permits ideal energy collection.

Since the cell includes two ports 18, 20 in the side wall 14, the apparatus 50 of FIG. 2 includes separate source and detector reflectors 22, 24. The reflectors are provided as cylindrical lens 22, 24 between the source "S" and the inlet port 18, and between the outlet port 20 and the detector "D". The detector lens 24 is provided with a focal length that is greater than a focal length of the source lens 22.

Figure 3:
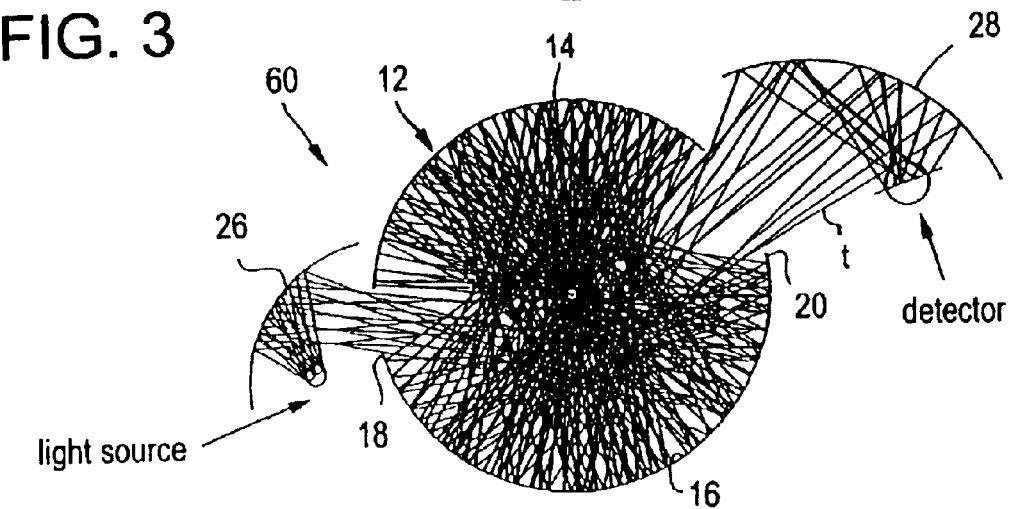
FIG. 3 is a schematic end plan view of a trace of a light ray directed by a set of launch and collection reflectors and completing multiple passes through a sample cell of an additional exemplary embodiment of an improved absorption spectroscopy apparatus constructed in accordance with the present invention.

FIG. 3 shows an additional exemplary embodiment of a spectroscopy apparatus 60 constructed in accordance with the present invention. The apparatus 60 is similar to the apparatus 50 of FIG. 2 such that similar elements have the same reference characters. However, the apparatus 60 further includes separate source and detector reflectors 26, 28 comprising mirrors instead of lens. As shown, the reflectors 26, 28 each comprise a segment of a cylinder. Preferably, the reflectors 26, 28 are molded and have polished inwardly-facing reflective surfaces, to simply manufacturing.

Figure 4:
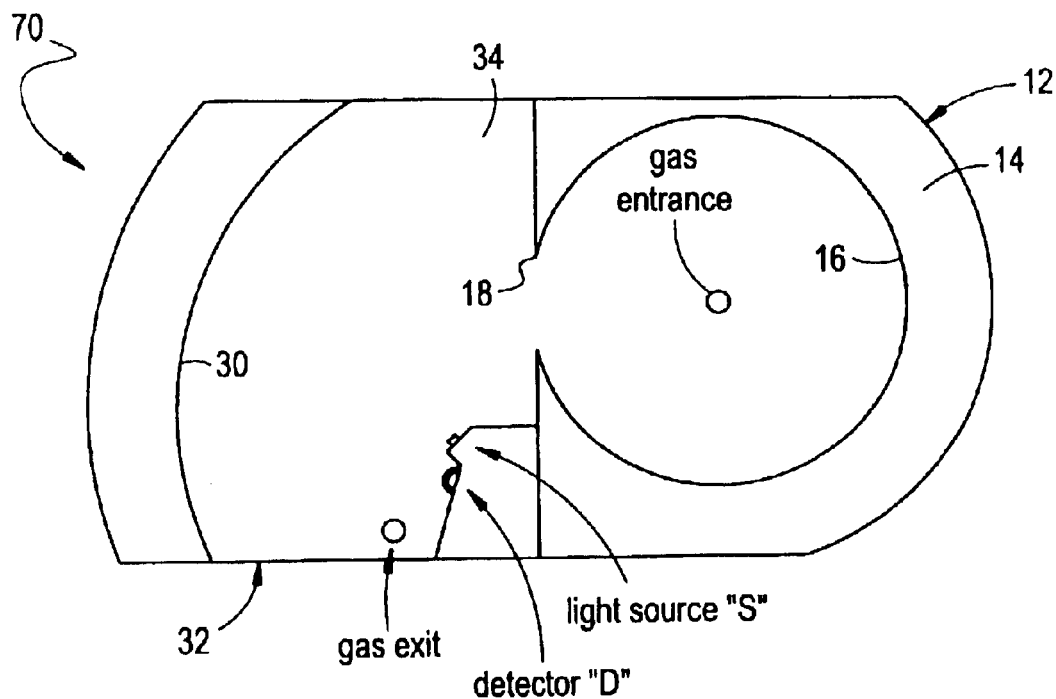
FIG. 4 is an end plan view of another exemplary embodiment of an improved absorption spectroscopy apparatus constructed in accordance with the present invention.
Figure 5:
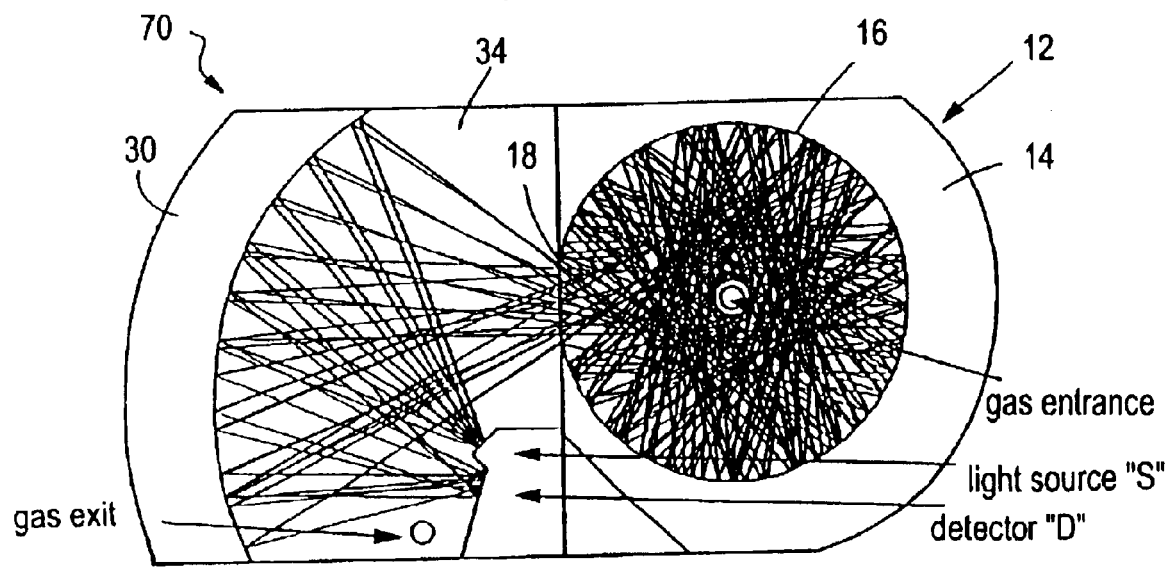
FIG. 5 is an end plan view showing a trace of a light ray passing through the absorption spectroscopy apparatus of FIG. 4.

Referring to FIGS. 4 and 5, a further exemplary embodiment of an absorption spectroscopy apparatus 70 constructed in accordance with the present invention is shown. The apparatus 70 is similar to the apparatus 60 of FIG. 3 such that similar element have the same reference characters. However, the cell 12 of the apparatus 70 includes a single port 18 in the side wall 14, and the source/detector reflector comprises a single source/detector mirror 30. The mirror 30 helps define a source/detector chamber 32 positioned against the sample cell 12. As shown, the end walls 34 of the sample chamber 12 extend over ends of the mirror 30 to help further define the enclosed chamber 32. The light source "S" and the detector "D" are housed within the chamber 32.

Figure 6:
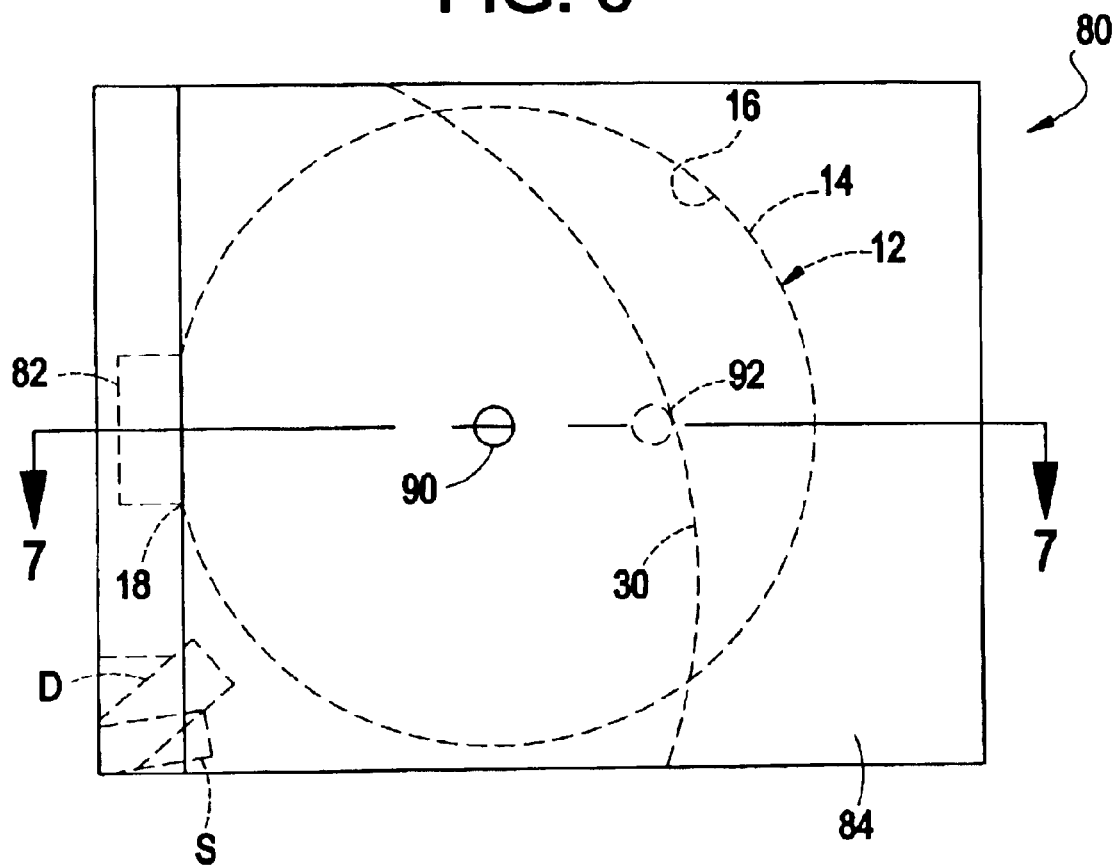
FIG. 6 is a side elevation view of an additional absorption cell constructed in accordance with the present invention.
Figure 7:
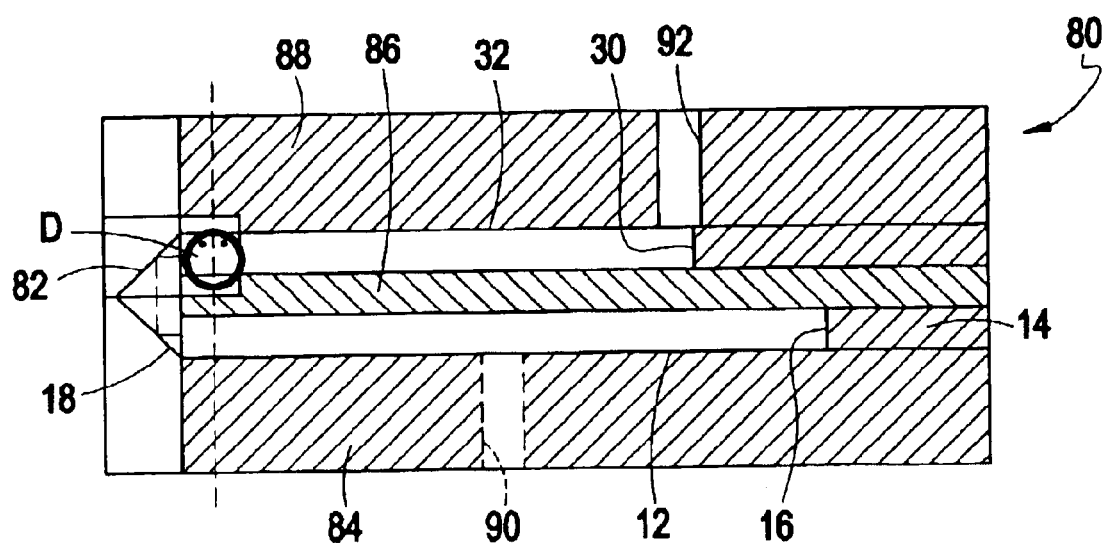
FIG. 7 is a sectional view taken along line 7—7 of the absorption cell of FIG. 6.
Figure 8:
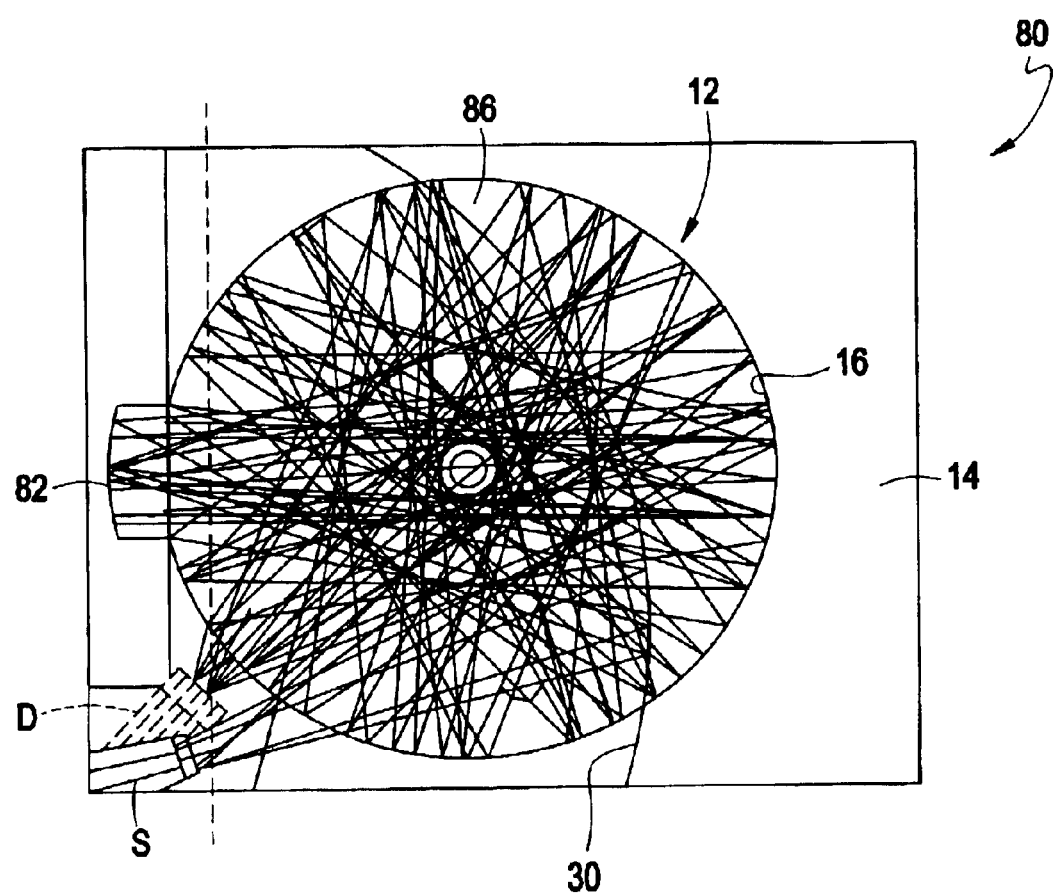
FIG. 8 is a side elevation view of the absorption cell of FIG. 6, wherein a side panel of the cell is removed and a trace of a light ray is shown directed by a single launch and collection mirror and an intermediate mirror and completing multiple passes through the absorption cell.

FIGS. 6 through 8 show another exemplary embodiment of an absorption spectroscopy apparatus 80 constructed in accordance with the present invention. The apparatus 80 is similar to the apparatus 70 of FIGS. 4 and 5, such that similar element have the same reference characters. However, the source/detector chamber 32 is "folded", or stacked, on the sample cell 12, and the apparatus 80 further includes an intermediate reflector 82 for reflecting energy from the source/detector mirror 30 into the port 18 of the sample cell 12, and from the port 18 of the sample cell 12 to the source/detector mirror 30. The apparatus 80 also includes three end walls 84, 86, 88, with two of the end walls 84, 88 defining respectively a sample inlet 90 and a sample outlet 92.

The present invention, therefore, provides an improved "multi-pass" sample cell that causes light to pass through a very large percentage of a sample contained in the cell. The improved sample cell prevents the loss of significant amounts of light through ends of the cell and increases the throughput of the cell. In addition, the improved cell is compact, robust, and relatively easy to manufacture.

Certain modifications and improvements to the exemplary embodiments of the present invention will occur to those skilled in the art upon a reading of the foregoing description. It should be understood that all such modifications and improvements have been deleted herein for the sake of conciseness and readability but are properly within the scope of the present invention as recited in the following claims.

What is claimed is:

1. An absorption spectroscopy apparatus having a fluid inlet and a fluid outlet and comprising:
   a sample cell including an axis, a side wall having at least one curved reflective surface arrayed about the axis and facing inwardly with respect to the axis such that a beam of energy directed against a predetermined location on the reflective surface is reflected back and forth off the reflective surface and remains in substantially the same plane while inside the cell, and at least one port in the sidewall, and end walls closing ends of the side wall and having flat reflective surfaces facing inwardly with respect to the cell and lying in a plane extending substantially perpendicular to the axis of the cell, wherein the cell has a height measured in a direction parallel to the axis substantially equal to a source length and an energy path in the cell is substantially perpendicular to the cell axis; and
   at least one source/detector reflector comprising a segment of a cylinder having a curved profile in a plane extending perpendicular to the axis of the cell, the reflector positioned with respect to the port of the cell to reflect energy through the port of the cell and against the predetermined location on the reflective surface of the side wall of the cell.

2. An absorption spectroscopy apparatus according to claim 1, wherein the reflective surface of the side wall of the cell has a circular profile in a plane extending perpendicular to the axis of the cell.

3. An absorption spectroscopy apparatus according to claim 1, wherein the reflective surface of the side wall of the cell has a flat profile in a plane extending parallel to the axis of the cell.

4. An absorption spectroscopy apparatus according to claim 1, wherein the port of the side wall of the cell comprises inlet and outlet ports, and the source/detector reflector comprises separate source and detector reflectors corresponding respectively to the inlet and the outlet ports.

5. An absorption spectroscopy apparatus according to claim 4, further comprising:
 a source for directing energy against the source reflector; and
 a detector for receiving energy from the detector reflector.

6. An absorption spectroscopy apparatus according to claim 1, further comprising an intermediate reflector positioned with respect to the port of the cell and the emitter/detector reflector to reflect energy from the emitter/detector reflector through the port of the cell and against the predetermined location on the reflective surface of the side wall of the cell.

7. An absorption spectroscopy apparatus according to claim 1, wherein the reflective surfaces of the end walls are polished.

8. An absorption spectroscopy apparatus according to claim 1, wherein the end walls are molded.

9. An absorption spectroscopy apparatus according to claim 1, wherein the end walls include the fluid inlet and the fluid outlet of the apparatus.

10. An absorption spectroscopy apparatus according to claim 1, wherein the side wall is molded.

11. An absorption spectroscopy apparatus according to claim 1, wherein the reflective surface of the side wall is polished.

12. An absorption spectroscopy apparatus according to claim 1, further comprising a light transmissive window positioned within the port of the side wall.

13. An absorption spectroscopy apparatus according to claim 1, further comprising:
 a source for directing energy against the at least one source/detector reflector; and
 a detector for receiving energy from the at least one source/detector reflector.

14. An absorption spectroscopy apparatus according to claim 1, wherein the port of the side wall of the cell comprises a single inlet/outlet port, and the source/detector reflector comprises a single source/detector reflector, and the apparatus further comprises a source for directing energy against the source/detector reflector, and a detector for receiving energy from the source/detector reflector.

15. An absorption spectroscopy apparatus according to claim 1, further comprising a source for directing energy against the at least one source/detector reflector, wherein the source provides infrared energy.

16. An absorption spectroscopy apparatus according to claim 1, wherein the source/detector reflector is polished.

17. An absorption spectroscopy apparatus according to claim 1, wherein the source/detector reflector is molded.

18. A sample cell for an absorption spectroscopy apparatus comprising:
 a side wall having,
  at least one curved reflective surface facing inwardly with respect to an axis of the sample cell such that a beam of energy directed against a predetermined location on the reflective surface is reflected back and forth off the reflective surface and inside the sample cell, and
  at least one port; and
 end walls closing opposing ends of the side wall and having substantially flat reflective surfaces facing inwardly with respect to the cell and extending substantially normal with respect to the axis such that a beam of energy reflected back and forth off the reflective surface of the side wall and inside the sample cell remains in substantially the same plane while inside the cell, wherein the cell has a height measured in a direction parallel to the axis substantially equal to a source length.

19. A sample cell according to claim 18, wherein the reflective surfaces of the end walls are polished.

20. A sample cell according to claim 18, wherein the end walls are molded.

21. A sample cell according to claim 18, wherein the reflective surface of the side wall is curved.

22. A sample cell according to claim 18, wherein the reflective surface of the side wall has a circular profile in a plane extending parallel with the reflective surfaces of the end walls of the cell.

23. A sample cell according to claim 18, wherein the reflective surface of the side wall has a flat profile in a plane extending parallel to the axis of the cell.

24. A sample cell according to claim 18, wherein the side wall is molded.

25. A sample cell according to claim 18, wherein the reflective surface of the side wall is polished.

26. A sample cell according to claim 18, further comprising a light transmissive window positioned within the port of the side wall.

27. An absorption spectroscopy apparatus including a sample cell according to claim 18, and further comprising at least one source/detector reflector having a curved profile in a plane extending perpendicular to the axis of the sample cell, the reflector positioned with respect to the port of the side wall of the sample cell to reflect energy through the port and against the predetermined location on the reflective surface of the side wall.

28. An absorption spectroscopy apparatus according to claim 27, wherein the port of the side wall of the sample cell comprises inlet and outlet ports, and the source/detector reflector comprises separate source and detector reflectors corresponding respectively to the inlet and the outlet ports.

29. An absorption spectroscopy apparatus according to claim 28, further comprising:
 a source for directing energy against the source reflector, and
 a detector for receiving energy from the detector reflector.

30. An absorption spectroscopy apparatus according to claim 28, further comprising:
 a source for directing energy against the at least one source/detector reflector; and
 a detector for receiving energy from the at least one source/detector reflector.

31. An absorption spectroscopy apparatus according to claim 28, wherein the port of the side wall of the cell comprises a single inlet/outlet port, and the source/detector reflector comprises a single source/detector reflector, and the apparatus further comprises a source for directing energy against the source/detector reflector, and a detector for receiving energy from the source/detector reflector.

32. An absorption spectroscopy apparatus according to claim 28, further comprising a source for directing energy against the at least one source/detector reflector, wherein the source provides infrared energy.

33. An absorption spectroscopy apparatus according to claim 28, wherein the source/detector reflector comprises a segment of a cylinder.

34. An absorption spectroscopy apparatus according to claim 28, wherein the source/detector reflector is polished.

35. An absorption spectroscopy apparatus according to claim 28, wherein the source/detector reflector is molded.

36. An absorption spectroscopy apparatus according to claim 27, further comprising an intermediate reflector positioned with respect to the port of the side wall of the sample cell and the emitter/detector reflector to reflect energy from the emitter/detector reflector through the port of the cell and against the predetermined location on the reflective surface of the side wall of the cell.

* * * * *